US012624370B2

(12) United States Patent
El Hassan et al.

(10) Patent No.: US 12,624,370 B2
(45) Date of Patent: May 12, 2026

(54) METHOD FOR TREATING RECYCLED AGGREGATES VIA MICROBIAL-INDUCED CALCITE PRECIPITATION

(71) Applicant: United Arab Emirates University, Al Ain (AE)

(72) Inventors: Hilal El Hassan, Al Ain (AE); Tamer El Maaddawy, Al Ain (AE); Ashraf Aly Hassan, Al Ain (AE); Mohammed Alzard, Al Ain (AE)

(73) Assignee: United Arab Emirates University, Al Ain (AE)

( * ) Notice: Subject to any disclaimer, the term of this patent is extended or adjusted under 35 U.S.C. 154(b) by 283 days.

(21) Appl. No.: 18/219,445

(22) Filed: Jul. 7, 2023

(65) Prior Publication Data

US 2025/0011818 A1 Jan. 9, 2025

(51) Int. Cl.
| | |
|---|---|
| *C04B 18/167* | (2023.01) |
| *C04B 20/10* | (2006.01) |
| *C04B 103/00* | (2006.01) |
| *C12P 3/00* | (2006.01) |

(52) U.S. Cl.
CPC .............. *C12P 3/00* (2013.01); *C04B 18/167* (2013.01); *C04B 20/107* (2013.01)

(58) Field of Classification Search
CPC ....... C12P 3/00; C04B 18/167; C04B 20/107; C04B 2103/0001
See application file for complete search history.

(56) References Cited

PUBLICATIONS

Zhang D. et al—"A Recycled Concrete And A Preparation Method Thereof", CN 111320429 A—Pub. date 06/23/202; English machine translation, total pp. 1-15. (Year: 2020).*
Pungrasmi W. et al., "Evaluation of Microencapsulation Techniques for MICP Bacterial Spores Applied in Self-Healing Concrete", Scientific Reports, Published online: 2019, 9:12484 (https://doi.org/10.1038/s41598-019-49002-6), total pp. 1-10. (Year: 2019).*
Che X-J, CN 114436601 A—"A Regenerated Aggregate Self-compacting Concrete And Its Preparation", Published on May 6, 2022, An English machine translation attached, total pp. 1-11. (Year: 2022).*
Arulraj et al., IN 201641009745 A—"Preparing self-healing bio-material agent comprising concrete, fly ash, gypsum or any other construction related material, for treating cracks in concrete", PUB. Jul. 7, 2017, Total pp. 1-2. (Year: 2017).*

* cited by examiner

*Primary Examiner* — Satyendra K Singh
(74) *Attorney, Agent, or Firm* — Hayes Soloway, PC

(57) ABSTRACT

Novel method to enhance the properties of recycled concrete aggregates by microbial-induced calcite precipitation. The present invention utilizes a microbial-induced calcium carbonate precipitation (MICP) as a novel treatment process to enhance the properties of RCA. The MICP application of the present invention is a natural process where bacteria produce calcium carbonate during their metabolic activities.

14 Claims, 3 Drawing Sheets

METHOD FOR TREATING RECYCLED AGGREGATES VIA MICROBIAL-INDUCED CALCITE PRECIPITATION

TECHNICAL FIELD

The present invention relates to a novel method to enhance the properties of recycled concrete aggregates via microbial-induced calcium carbonate precipitation.

BACKGROUND

Rapid growth in the global population and economy has led to increasing demand for infrastructure development. As the most widely used construction material, concrete is responsible for the depletion of natural resources. Its main component by mass and volume is aggregates. They are sourced from non-renewable natural resources. Meanwhile, construction and demolition activities have led to the generation of a significant amount of concrete waste. This type of waste is called construction and demolition waste (CDW). Typically, CDW is sent to landfills for disposal, which is not a sustainable solution owing to the scarcity of stockpiling sites and environmental consequences. Thus, there is a need to beneficially reutilize CDW. One such means is to reuse it as aggregates, denoted as recycled concrete aggregates (RCA).

RCA has been presented as an attractive alternative to replace natural aggregates (NA) in concrete production and has been praised by several scholars. However, the challenge is that the physical properties of RCA are inferior to those of NA, due to the attached mortar on its surface and its high porosity. This is caused by the high percentage of capillary pores and microcracks on the surface and often in the internal transition zone (ITZ). As a result, concrete made with RCA experienced reductions in workability, compressive strength, splitting tensile strength, and flexural strength, among other properties. This fact has hindered the adoption of RCA by the concrete industry. Therefore, RCA requires pretreatment or preprocessing to enhance its properties prior to utilizing it in concrete products. Different treatment methods have been established. These can be categorized as enhancing the . . . properties of RCA, strengthening the attached mortar, or a combination of both. Treatments related to enhancing the properties of RCA include removal of the attached mortar, autogenous cleaning, mechanical grinding, heat grinding, acid treatment, and thermochemical treatment. Conversely, strengthening the attached mortar treatments comprises pozzolanic slurry, emulsion polymer, carbonation curing, cement slurry coating, sodium silicate solution, and bio-deposition of calcium carbonate.

Microbial-induced calcium carbonate precipitation (MICP) has been recently explored as a promising technology for improving the engineering properties of different construction materials. This technology is based on a natural process whereby bacterial cells produce inorganic minerals as part of their basic metabolic activities. MICP has been used extensively in the production of self-healing concrete and mortars to seal cracks. Yet, there is significant room to refine this technique to yield the maximum benefit of MICP. Therefore, there is a need for a new environmentally friendly simple method that can used at room temperature with no energy consumption, utilizing a variety of microorganism for medical and industrial applications.

SUMMARY

The present invention utilizes a microbial-induced calcium carbonate precipitation (MICP) as a novel treatment process to enhance the properties of RCA. The MICP application of the present invention is a natural process where bacteria produce calcium carbonate during their metabolic activities.

The utility of this invention toward a circular economy is threefold. First, the product of this treatment method, i.e., treated RCA, will replace NA, thereby preserving non-renewable natural resources. Second, the use of RCA, which is inherently from construction and demolition waste (CDW), will serve to recycle such waste materials rather than disposing of them in stockpiles. And third, the utilization of CDW will alleviate the demand for land needed for stockpiling.

In one embodiment, disclosed herein is a method for enhancing the properties of RCA, comprising the application of microbial-induced calcite precipitate to the RCA by the application of a treatment agent comprising a bacterial strain, an immobilization gel comprising alginate, nutrients and ureas, and a calcium source.

In another embodiment, the method comprises the treatment application of two solutions selected from the group consisting of an immobilization gel and a calcium source.

In one aspect, the calcium source is calcium chloride.

In some aspects, the bacterial strain can be a bacterium or a lyophilized bacterium.

In another aspects, the bacterial strain is gram-positive.

In a further aspect, the bacterial strain is aerobic.

In a preferred aspect, the bacterial strain includes bacteria that can form a carbonate precipitate in an alkaline medium.

In a more preferred aspect, the bacterial strain includes genus *Lysinibacillus* and genus *Priestia.*

In a most preferred aspect, the bacterial strain may include one or more strains including *Lysinibacillus sphaericus* and *Priestia megaterium.*

In another aspect, the calcium source includes an inorganic compound.

In one example, the calcium source comprises a compound including calcium.

In a preferred example, the calcium source comprises one or more compounds selected from the group consisting of calcium chloride, calcium acetate, and calcium lactate.

In some examples, the base concentration of calcium chloride is approximately 41.625 g/L.

In some examples, the concentration of calcium chloride ranges from approximately ×1 to ×20 the base concentration of calcium chloride.

In some examples, the concentration of calcium chloride preferably ranges from approximately ×12 to ×20 the base concentration of calcium chloride.

In some examples, the concentration of calcium chloride more preferably ranges from approximately ×14 to ×20 the base concentration of calcium chloride.

In some examples, the concentration of calcium chloride most preferably is approximately ×20 the base concentration of calcium chloride.

In another example, the immobilization gel comprises a compound including urea.

In some examples, the base concentration of urea is 41.625 g/L.

In some examples, the concentration of urea ranges from approximately ×1 to ×20 the base concentration of urea.

In preferred examples, the immobilization gel comprises nutrients for bacterial growth including an organic compound and a phosphorus compound.

In some examples, the nutrients comprise peptone, sodium chloride, HM peptone B, and yeast extract.

In another aspect, the immobilization gel comprises sodium alginate.

In some examples, the immobilization gel is made of sodium alginate at a concentration of approximately 5% weight by volume (w/v).

In some embodiments, the RCA comprises recycled construction and demolition concrete waste formed into coarse aggregates having a particle size equal or larger than approximately 5 mm.

In certain embodiments, the application of two solutions comprises a treatment selected from the group consisting of spraying, soaking, and a sequential combination of spraying and soaking.

In some aspects, the immobilization gel is first sprayed onto the RCA and then the calcium chloride is sprayed.

In some aspects, the RCA is first soaked in the immobilization gel followed by soaking in the calcium chloride solution.

In some aspects, the RCA is first soaked in the calcium chloride solution followed by soaking in the immobilization gel.

In some aspects, the immobilization gel is first sprayed onto the RCA, and then the RCA is soaked in the calcium chloride solution.

In some aspects, the calcium chloride solution is first sprayed onto the recycled concrete aggregates, and then the RCA is soaked in the immobilization gel.

In some aspects, the RCA is soaked in a solution comprising the immobilization gel and calcium chloride.

In some aspects, cracks in the RCA are sealed during the treatment.

In some aspects, cracks in the RCA are sealed during service.

In some aspects, porosity and water absorption of the RCA are reduced by the treatment compared to untreated RCA.

In some examples, porosity and water absorption are reduced to values ranging from approximately 0.5% to 6.2%.

In some examples, porosity and water absorption are preferably reduced to values ranging from approximately 0.5% to 3.0%.

In some examples, porosity and water absorption are more preferably reduced to values ranging from approximately 0.8% to 2.0%.

In some examples, porosity and water absorption are most preferably reduced to values ranging from approximately 0.8% to 1.2%.

In some aspects, the impact and abrasion resistance of the RCA after 500 revolutions utilizing to the Los Angeles Abrasion Value Test is enhanced following the treatment compared to untreated RCA.

In some examples, the impact and abrasion resistance test values range from 10% to 25% in mass loss.

In some examples, the impact and abrasion resistance test values preferably range from 15% to 21% in mass loss.

In some examples, the impact and abrasion resistance test values more preferably range from 15% to 18% in mass loss.

In some examples, the impact and abrasion resistance test values most preferably range from 14% to 15% in mass loss.

While the disclosure is susceptible to various modifications and alternative forms, specific aspects thereof are shown by way of example in the drawing and will herein be described in detail. It should be understood, however, that the drawings and detailed description presented herein are not intended to limit the disclosure to the particular aspects disclosed, but on the contrary, the intention is to cover all modifications, equivalents, and alternatives falling within the spirit and scope of the present disclosure as defined by the appended claims.

Other features and advantages of this invention will become apparent in the following detailed description of preferred aspects of this invention, taken with reference to the accompanying drawings.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DEFINITIONS

Figure 1:
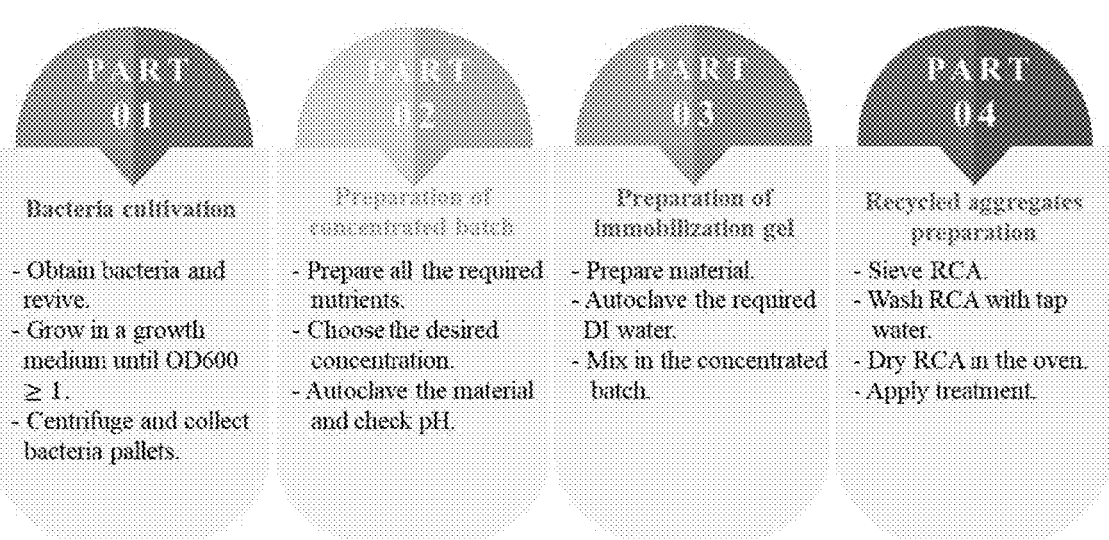
FIG. 1 provides a schematic summary of the methodology of the present invention.

As used in this description and the accompanying claims, the following terms shall have the meanings indicated, unless the context otherwise requires:

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "scaffold" in accordance with the present invention, includes scaffold, body, block, chip, substrate, matrix, or segment.

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

DETAILED DESCRIPTION

Concrete production is on the rise to meet the request due the ever-increasing population growth and economic development. It is a non-environment-friendly process whereby substantial amounts of natural resources are consumed in the production of its two main components, cement, and aggregates. As aggregates occupy at least 75% of the concrete volume, their replacement by greener alternatives is pivotal in enhancing the sustainability of the construction industry. The utilization of recycled concrete aggregates (RCA) from construction and demolition waste as a replacement for natural aggregates (NA) has been gaining momentum owing to its abundance and similarity to concrete. Yet, due to the high pore volume and attached old mortar, the properties of RCA are inferior to its NA counterpart. To promote the adoption of RCA in construction applications, its performance should be improved to be equivalent to that of NA.

A study was conducted to identify novel features of microbial-induced calcium carbonate precipitation (MICP) that have not been yet investigated, such as (1) utilizing sodium alginate to further enhance the MICP action; (2) exploring the effect of different concentrations of the materials required to carry out MICP; (3) employing different techniques to apply the MICP treatment; and (4) using these methods on RCA obtained from actual recycling plants. The use of such inorganic minerals can be applied to RCA to improve their overall physical properties by reducing the porosity and enhancing the quality of the attached mortar on the surface.

In some embodiments, the present invention utilizes MICP as an innovative treatment process that can be used to enhance the properties of RCA. This MICP application is a natural process where bacteria produce calcium carbonate during their metabolic activities. The contribution of this invention toward a circular economy is threefold. First, the product of this treatment method, i.e., treated RCA, will replace NA, thereby preserving non-renewable natural resources. Second, the use of RCA, which is inherently from construction and demolition waste (CDW), will serve to recycle such waste materials rather than disposing of them in stockpiles. Third, the utilization of CDW will alleviate the demand for land needed for stockpiling. The use of MICP to enhance the properties of RCA has not yet been fully explored by researchers.

In other embodiments, the present invention introduces a novel treatment method that utilizes MICP to enhance the properties of RCA. The treated aggregates are aimed at replacing natural aggregates in the production of concrete. This will simultaneously address multiple globally recognized problems, including the depletion of natural resources, emission of greenhouse gases, occupying of land as disposal sites for CDW, and amassing of construction wastes.

In one embodiment, disclosed herein is a method for enhancing the properties of RCA, comprising the application of microbial-induced calcite precipitate to the RCA by the application of a treatment agent comprising a bacterial strain, an immobilization gel comprising alginate, nutrient, and urea, and a calcium source.

In another embodiment, the method comprises the treatment application of two solutions selected from the group consisting of an immobilization gel and a calcium source.

In one aspect, the calcium source is calcium chloride.

In some aspects, the bacterial strain can be a bacterium or a lyophilized bacterium.

In another aspects, the bacterial strain is gram-positive.

In a further aspect, the bacterial strain is aerobic.

In a preferred aspect, the bacterial strain includes bacteria that can form a carbonate precipitate in an alkaline medium.

In a more preferred aspect, the bacterial strain includes genus *Lysinibacillus* and genus *Priestia*.

In a most preferred aspect, the bacterial strain may include one or more strains including *Lysinibacillus sphaericus* and *Priestia megaterium*.

In another aspect, the calcium source includes an inorganic compound.

In one example, the calcium source comprises a compound including calcium.

In a preferred example, the calcium source comprises one or more compounds selected from the group consisting of calcium chloride, calcium acetate, and calcium lactate.

In some examples, the base concentration of calcium chloride is approximately 41.625 g/L.

In some examples, the concentration of calcium chloride ranges from approximately ×1 to ×20 the base concentration of calcium chloride.

In some examples, the concentration of calcium chloride preferably ranges from approximately ×12 to ×20 the base concentration of calcium chloride.

In some examples, the concentration of calcium chloride more preferably ranges from approximately ×14 to ×20 the base concentration of calcium chloride.

In some examples, the concentration of calcium chloride most preferably is approximately ×20 the base concentration of calcium chloride.

In another example, the immobilization gel comprises a compound including urea.

In some examples, the base concentration of urea is 41.625 g/L.

In some examples, the concentration of urea ranges from approximately ×1 to ×20 the base concentration of urea.

In preferred examples, the immobilization gel comprises nutrients for bacterial growth including an organic compound and a phosphorus compound.

In some examples, the nutrients comprise peptone, sodium chloride, HM peptone B, and yeast extract.

In another aspect, the immobilization gel comprises sodium alginate.

In some examples, the immobilization gel is made of sodium alginate at a concentration that ranges approximately from 3% to 10%. weight by volume (w/v).

In some examples, the immobilization gel is made of sodium alginate at a preferred concentration of approximately 5% weight by volume (w/v).

In some embodiments, the RCA comprises recycled construction and demolition concrete waste formed into coarse aggregates having a particle size equal or larger than approximately 5 mm.

In certain embodiments, the application of two solutions comprises a treatment selected from the group consisting of spraying, soaking, and a sequential combination of spraying and soaking.

In some aspects, the immobilization gel is first sprayed onto the RCA and then the calcium chloride is sprayed.

In some aspects, the RCA is first soaked in the immobilization gel followed by soaking in the calcium chloride solution.

In some aspects, the RCA is first soaked in the calcium chloride solution followed by soaking in the immobilization gel.

In some aspects, the immobilization gel is first sprayed onto the RCA, and then the RCA is soaked in the calcium chloride solution.

In some aspects, the calcium chloride solution is first sprayed onto the recycled concrete aggregates, and then the RCA is soaked in the immobilization gel.

In some aspects, the RCA is soaked in a solution comprising the immobilization gel and calcium chloride.

In some aspects, cracks in the RCA are sealed during the treatment.

In some aspects, cracks in the RCA are sealed during service.

In some aspects, porosity and water absorption of the RCA are reduced by the treatment compared to untreated RCA.

In some examples, porosity and water absorption are reduced to values ranging from approximately 0.5% to 6.2%.

In some examples, porosity and water absorption are preferably reduced to values ranging from approximately 0.5% to 3.0%.

In some examples, porosity and water absorption are more preferably reduced to values ranging from approximately 0.8% to 2.0%.

In some examples, porosity and water absorption are most preferably reduced to values ranging from approximately 0.8% to 1.2%.

In some aspects, the impact and abrasion resistance of the RCA after 500 revolutions utilizing to the Los Angeles Abrasion Value Test is enhanced following the treatment compared to untreated RCA.

In some examples, the impact and abrasion resistance test values range from 10% to 25% in mass loss.

In some examples, the impact and abrasion resistance test values preferably range from 15% to 21% in mass loss.

In some examples, the impact and abrasion resistance test values more preferably range from 15% to 18% in mass loss.

In some examples, the impact and abrasion resistance test values most preferably range from 14% to 15% in mass loss.

In some examples, the application of the treatment methods enhances the properties of the RCA.

In some embodiments, the method of the present invention can be scaled up for industrial production.

In some embodiments, the use of bacteria that are capable of microbially inducing calcium carbonate precipitation on the surface of RCA reduce the porosity and improve the quality of the old mortar attached to the surface of the RCA. This leads to an overall enhancement in the physical properties of the RCA. Utilizing sodium alginate gel improves the process of MICP, yielding higher levels of enhancement in the properties of RCA.

Any bacterial strain capable of forming CaCO$_3$ precipitates (MICP) in an alkaline medium may be suitable as the bacterial strains used in the methods described herein. Non-limiting examples of MICP strains include: *Lysinibacillus sphaericus, Priestia megaterium, Bacillus sphaericus, Bacillus cohnii, Bacillus pseudofirmus, Bacillus subtilis, Bacillus alkalinitrilicus, Bacillus megaterium*, and *Sporosarcina pasteurii.*

In some embodiments, the method for enhancing the properties of RCA includes a concentrated batch that may include one or more bacterial strain, urea, and nutrients.

In some aspects, the concentrated batch may include pure concentrated bacteria.

In some aspects, the concentrated batch can be utilized at different concentrations of nutrients and urea.

In some aspects, the nutrients may include calcium chloride.

In some examples, the concentrated batch is prepared at a base concentration of ×1 using approximately 41.625 g/L of calcium chloride and urea respectively.

In some examples, in addition to the base concentration of ×1, different concentrations may be used, including, for example, ×2, ×3, ×4, ×5, ×6, ×7, ×8, ×9, ×10, ×11, ×12, ×13, ×14, ×15, ×16, ×17, ×18, ×19, and ×20, preferably, ×2, ×4, ×8, ×10, ×12, ×14, ×16, and ×20, In some examples, in addition to the base concentration of ×1, different concentrations may be used, including, more preferably, ×12, ×14, ×16, and ×20.

In some examples, in addition to the base concentration of ×1, different concentrations may be used, including, most preferably, ×14, ×16, and ×20.

In some embodiments, the method of the present invention comprises six treatment techniques, including spraying, soaking, and a sequential combination of spraying and soaking two solutions comprising an immobilization gel and calcium chloride.

In some examples, the six treatment techniques applied to the bacterial strains include: (1) soaking in immobilization gel and then soaking in calcium chloride solution; (2) soaking in calcium chloride solution and then in immobilization gel; (3) spraying the immobilization gel and then soaking in calcium chloride solution; (4) spraying the calcium chloride solution and then soaking in immobilization gel; (5) spraying the immobilization gel and then spraying the calcium chloride solution; and (6) soaking in a mixture of immobilization gel and calcium chloride.

In some embodiments, the application of a treatment technique results in mass gain of the RCA.

In some examples, the preferred concentration of the concentrated batch to obtain mass gain includes ×10, ×11, ×12, ×13, ×14, ×15, ×16, ×17, ×18, ×19, and ×20.

In some examples, the more preferred concentration of the concentrated batch to obtain mass gain includes ×10, ×12, ×14, ×16, ×18, and ×20.

In some examples, the most preferred concentration of the concentrated batch to obtain mass gain includes ×12, ×14, ×16, ×18, and ×20.

In some embodiments, the application of a treatment technique reduces the porosity and water absorption of the RCA.

In some examples, the preferred concentration of the concentrated batch resulting in a reduction of the porosity and water absorption of the RCA includes ×12, ×13, ×14, ×15, ×16, ×17, ×18, ×19, and ×20.

In some examples, the more preferred concentration of the concentrated batch resulting in a reduction of the porosity and water absorption of the RCA includes ×12, ×14, ×16, ×18, and ×20.

In some examples, the more preferred concentration of the concentrated batch resulting in a reduction of the porosity and water absorption of the RCA includes ×12, ×14, and ×20.

In some embodiments, the application of a treatment technique results in enhancement of the impact and abrasion resistance of the RCA after 500 revolutions utilizing to the Los Angeles Abrasion Value Test compared to untreated RCA.

In some aspects, this method will enable the industry to improve the quality of the RCA and accelerate the efforts of replacing NA with RCA for different applications, especially in the production of concrete. This innovative treatment method provides a practical and environment-friendly solution to the global issues of depletion of natural resources, the increasing levels of greenhouse gas emissions, the use of vast areas of land for landfills, and the accumulation of construction and demolition waste.

While the disclosure is susceptible to various modifications and alternative forms, specific aspects thereof are shown by way of example in the drawing and will herein be described in detail. It should be understood, however, that the drawings and detailed description presented herein are not intended to limit the disclosure to the particular aspects disclosed, but on the contrary, the intention is to cover all modifications, equivalents, and alternatives falling within the spirit and scope of the present disclosure as defined by the appended claims.

Other features and advantages of this invention will become apparent in the following detailed description of preferred aspects of this invention, taken with reference to the accompanying drawings.

EXPERIMENTAL EXAMPLES

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Performance Evaluation of the Treated RCA

Treatment Procedure

Figure 2:
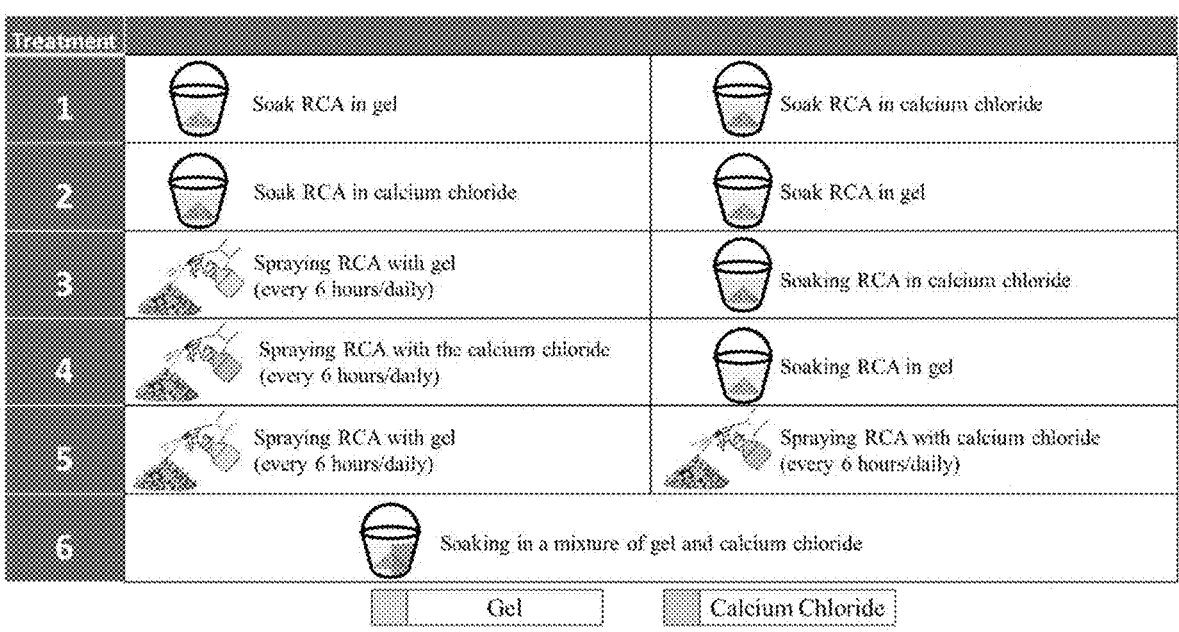
FIG. 2 provides different types of treatment applications.

Six different techniques were investigated to evaluate the calcium carbonate ($CaCO_3$) precipitation capacity of the two types of bacteria. Since calcium chloride is the reactant responsible for the formation of the calcium carbonate, it was isolated from the immobilization gel. As such, two solutions were used in each treatment technique: the immobilization gel and calcium chloride (i.e., calcium source). Each treatment can be applied for up to six days. The procedure followed in each treatment is presented in FIG. 2 and is described as follows: (1) Soaking in immobilization gel and then soaking in calcium chloride solution; (2) Soaking in calcium chloride solution and then in immobilization gel; (3) Spraying the immobilization gel and then soaking in calcium chloride solution; (4) Spraying the calcium chloride solution and then soaking in immobilization gel; (5) Spraying the immobilization gel and then spraying the calcium chloride solution; (6) Soaking in a mixture of immobilization gel and calcium chloride.

The configuration of these treatment methods aims to study the effect of the two application methods, i.e., soaking and spraying, of the immobilization gel and calcium source and examine the influence of the application sequence on the properties of the RCA. The difference in treatments also serves to provide alternatives based on the needs of the user. For example, in concrete recycling plants where RCA are produced, treatments involving spraying might be the best treatments to apply, as they can be easily incorporated into the current recycling process.

Example 1—Mass Gain

Table 1 presents the mass gain of RCA samples subjected to the six treatment techniques (1-6), as described above. For these samples, the treatment included the bacterial solution and excluded the sodium alginate immobilization gel. Both types of bacteria, DSM 28 and DSM 32, highlighted a general increase in mass gain with higher concentrations. Yet, a comparison to the results of RCA samples treated in the presence of the sodium alginate immobilization gel (Table 2) showed that the latter was superior. This provides evidence of the ability of the immobilization gel to enhance the mass gain regardless of the treatment applied. As such, higher concentrations (up to ×20) were only applied to the treatments in the presence of the sodium alginate immobilization gel.

TABLE 1

Mass gain for the six treatment techniques at different concentrations without the sodium alginate immobilization gel.

| | | Bacteria | |
|---|---|---|---|
| Treatment | Concentration | DSM 28 | DSM 32 |
| 1 | ×0.5 | 0.13 | 0.35 |
| | ×1.0 | 0.58 | 0.35 |
| | ×2.0 | 0.40 | 0.61 |
| 2 | ×0.5 | 0.19 | 0.12 |
| | ×1.0 | 0.37 | 0.21 |
| | ×2.0 | 0.31 | 0.26 |
| 3 | ×0.5 | 0.13 | 0.08 |
| | ×1.0 | 0.05 | 0.04 |
| | ×2.0 | 0.68 | 0.87 |
| 4 | ×0.5 | 0.18 | 0.07 |
| | ×1.0 | 0.25 | 0.23 |
| | ×2.0 | 0.50 | 0.25 |
| 5 | ×0.5 | 0.17 | 0.11 |
| | ×1.0 | 0.19 | 0.36 |
| | ×2.0 | 0.52 | 0.52 |
| 6 | ×0.5 | 0.16 | 0.22 |
| | ×1.0 | 0.93 | 0.24 |
| | ×2.0 | 0.04 | 0.03 |

TABLE 2

Mass gain for the six treatment techniques at different concentrations with the sodium alginate immobilization gel.

| | | Bacteria | |
|---|---|---|---|
| Treatment | Concentration | DSM 28 | DSM 32 |
| 1 | ×1 | 0.56 | 0.49 |
| | ×2 | 0.94 | 0.89 |
| | ×4 | 1.12 | 1.75 |
| | ×6 | 2.15 | 2.62 |
| | ×8 | 2.87 | 2.71 |
| | ×10 | 3.42 | 3.23 |
| | ×12 | 4.61 | 4.31 |
| | ×14 | 4.23 | 4.03 |
| | ×16 | 2.50 | 2.62 |
| | ×20 | 2.52 | 2.28 |
| 2 | ×1 | 0.09 | 0.34 |
| | ×2 | 0.34 | 0.57 |
| | ×4 | 0.84 | 1.05 |
| | ×6 | 1.35 | 1.16 |
| | ×8 | 1.50 | 1.32 |
| | ×10 | 2.16 | 1.18 |
| | ×12 | 1.75 | — |
| | ×14 | — | — |
| | ×16 | — | — |
| | ×20 | — | — |
| 3 | ×1 | 0.81 | 0.27 |
| | ×2 | 0.81 | 1.05 |
| | ×4 | 1.57 | 1.50 |
| | ×6 | 2.33 | 2.19 |
| | ×8 | 3.01 | 2.82 |
| | ×10 | 3.12 | 2.46 |

US 12,624,370 B2

11

TABLE 2-continued

Mass gain for the six treatment techniques at different concentrations with the sodium alginate immobilization gel.

| | | Bacteria | |
| Treatment | Concentration | DSM 28 | DSM 32 |
| --- | --- | --- | --- |
| | ×12 | 4.25 | 2.80 |
| | ×14 | 4.42 | 5.42 |
| | ×16 | 2.65 | 2.47 |
| | ×20 | 2.04 | 2.10 |
| 4 | ×1 | 0.58 | 0.27 |
| | ×2 | 0.37 | 1.05 |
| | ×4 | 1.38 | 1.50 |
| | ×6 | 1.80 | 2.19 |
| | ×8 | 3.06 | 2.83 |
| | ×10 | 2.65 | 2.83 |
| | ×12 | 2.26 | 2.57 |
| | ×14 | — | — |
| | ×16 | — | — |
| | ×20 | — | — |
| 5 | ×1 | 0.61 | 0.31 |
| | ×2 | 0.65 | 0.61 |
| | ×4 | 1.26 | 0.77 |
| | ×6 | 1.21 | 1.47 |
| | ×8 | 2.68 | 1.48 |
| | ×10 | 3.00 | 1.25 |
| | ×12 | 3.10 | — |
| | ×14 | 2.90 | — |
| | ×16 | — | — |
| | ×20 | — | — |
| 6 | ×1 | 0.18 | 0.29 |
| | ×2 | 1.03 | 0.51 |
| | ×4 | 1.58 | 1.00 |
| | ×6 | 2.04 | 1.92 |
| | ×8 | 2.09 | 2.35 |
| | ×10 | 2.82 | 3.01 |
| | ×12 | 4.19 | 3.54 |
| | ×14 | 4.70 | 3.87 |
| | ×16 | 5.10 | 4.68 |
| | ×20 | 5.90 | 5.21 |

Table 2 shows that increasing the concentration of nutrients, urea, and calcium led to an increase in the mass gain of RCA. It should be noted that the concentrations were only increased as they increased the mass gain, i.e., if the mass gain remained the same or decreased, no further increase in the concentration was investigated. As such, the values for some concentrations were left blank (-). Results highlight that the optimal concentration, i.e., yielding the highest mass gain, differed from one treatment to another. For treatment 1, a concentration of ×12 was optimum for both types of bacteria (DSM 28 and DSM 32), whereas, for treatment 2, the optimal concentration was ×10 and ×8 for DSM 28 and DSM 32, respectively. For treatments 3 and 4, concentrations of ×14 and ×8 provided the highest mass gain for the two types of bacteria, correspondingly. Meanwhile, treatment 5 was performed optimally at concentrations of ×12 and ×8 for DSM 28 and DSM 32, respectively. Finally, treatment 6 showed an increasing trend of mass gain as the concentration of the materials increased for DSM 28 and DSM 32. The highest mass gain was at a concentration of ×20. Among the six treatment techniques under investigation, treatments 1, 3, and 6 presented the highest mass gain, regardless of the type of bacteria. This shows that optimal calcium carbonate precipitation, represented by high mass gain, was attained in treatments that either soaked the RCA in the immobilization gel and calcium chloride simultaneously (treatment 6) or those that applied the immobilization gel first, whether by spraying or soaking, followed by soaking in calcium chloride (treatments 1 and 3). Additionally, the best treatment technique for DSM 28 was treatment 6 with a concentration of ×20 (5.90%, by mass), while that for DSM 32 was treatment 3 with a concentration of ×14 (5.42%, by mass).

Example 2—Water Absorption

TABLE 3

Water absorption percentage for the treated samples with DSM 28 and DSM 32.

| | | Bacteria | |
| Treatment | Concentration | DSM 28 | DSM 32 |
| --- | --- | --- | --- |
| 1 | ×1 | 5.0 | 6.0 |
| | ×2 | 4.8 | 5.6 |
| | ×4 | 4.7 | 5.2 |
| | ×6 | 4.2 | 3.6 |
| | ×8 | 3.6 | 3.7 |
| | ×10 | 3.3 | 2.6 |
| | ×12 | 2.9 | 1.1 |
| | ×14 | 3.0 | 2.0 |
| | ×16 | 3.8 | 4.0 |
| | ×20 | 3.8 | 3.9 |
| 2 | ×1 | 5.8 | 6.2 |
| | ×2 | 5.6 | 5.8 |
| | ×4 | 5.4 | 5.6 |
| | ×6 | 4.9 | 4.4 |
| | ×8 | 4.7 | 3.3 |
| | ×10 | 4.3 | — |
| | ×12 | 4.5 | — |
| | ×14 | — | — |
| | ×16 | — | — |
| | ×20 | — | — |
| 3 | ×1 | 4.0 | 6.1 |
| | ×2 | 4.0 | 5.0 |
| | ×4 | 3.8 | 4.5 |
| | ×6 | 3.6 | 3.5 |
| | ×8 | 3.0 | 2.8 |
| | ×10 | 2.9 | 3.0 |
| | ×12 | 2.1 | 2.9 |
| | ×14 | 2.0 | 1.6 |
| | ×16 | 3.4 | 3.3 |
| | ×20 | 3.8 | 3.6 |
| 4 | ×1 | 5.5 | 5.8 |
| | ×2 | 5.7 | 5.0 |
| | ×4 | 4.7 | 4.5 |
| | ×6 | 3.8 | 3.5 |
| | ×8 | 3.3 | 2.4 |
| | ×10 | 3.6 | 2.4 |
| | ×12 | 3.7 | 2.8 |
| | ×14 | — | — |
| | ×16 | — | — |
| | ×20 | — | — |
| 5 | ×1 | 5.2 | 5.8 |
| | ×2 | 5.0 | 5.2 |
| | ×4 | 4.6 | 5.0 |
| | ×6 | 4.8 | 4.6 |
| | ×8 | 2.6 | 4.3 |
| | ×10 | 2.5 | 4.8 |
| | ×12 | 2.4 | — |
| | ×14 | 2.5 | — |
| | ×16 | — | — |
| | ×20 | — | — |
| 6 | ×1 | 5.8 | 5.2 |
| | ×2 | 3.4 | 4.0 |
| | ×4 | 3.3 | 3.6 |
| | ×6 | 3.1 | 3.0 |
| | ×8 | 3.0 | 2.5 |
| | ×10 | 2.4 | 1.8 |
| | ×12 | 1.8 | 1.7 |
| | ×14 | 1.7 | 1.6 |
| | ×16 | 1.6 | 1.3 |
| | ×20 | 0.8 | 1.2 |

Water absorption was used to prove the efficiency of the MICP treatment techniques. It should be noted that the water absorption of untreated RCA was 6.67%. As such, RCA

13 | 14 values less than 6.67% were indicative of a decrease in the void content due to calcium carbonate precipitation and an improvement in performance, and vice versa. The water absorption of the treated RCA using DSM 28 and DSM 32 (immobilized in the sodium alginate gel) is presented in Table 4. For DSM 28 and DSM 32, values ranged from 0.8 to 5.8% and 1.1 to 6.2%, respectively. In fact, treatment 6 showed the lowest water absorption results, followed by treatments 1 and 3, regardless of the bacteria used. Such findings are synonymous with those of mass gain, highlighting the ability of these treatments to reduce the void content through calcium carbonate precipitation.

Example 3—Impact and Abrasion Resistance

Table 4 presents the abrasion mass loss of as-received, untreated RCA. The untreated RCA experienced a 33% mass loss due to abrasion after 500 revolutions. This value serves as a reference to be compared to the abrasion mass loss of RCA after treatment. For each type of bacteria, three (3) treatments were selected based on their superior mass gain and water absorption results, i.e., treatments 1, 3, and 6. The concentrations were chosen based on those that resulted in the highest mass gains. Table 5 shows the abrasion mass loss of RCA treated with each type of bacteria (DSM 28 and DSM 32) and following the three treatment techniques. The results show that all treatment methods enhanced the RCA abrasion resistance, evidenced by the lower abrasion mass loss compared to that of the untreated RCA. For treatments 1 and 6, DSM 28 provided superior abrasion resistance (i.e., lower abrasion mass loss) to DSM 32, while the opposite scenario was noted for treatment 3. Furthermore, among the different treatment techniques, treatment 6 with DSM 28 provided the best abrasion resistance (i.e., lowest mass loss). This is in line with the mass gain and water absorption results. Such enhancement in abrasion resistance is owed to the precipitation of calcium carbonate on the surface and possibly inside the treated RCA samples.

TABLE 4

Los Angeles Abrasion Value for untreated recycled aggregates

| | Revolutions | % Loss |
| --- | --- | --- |
| RA | 0 | 0 |
| | 100 | 11.6 |
| | 200 | 16.1 |
| | 300 | 22.5 |
| | 400 | 27.2 |
| | 500 | 33.0 |

TABLE 5

Summary of Los Angeles Abrasion Value for selected treatment methods at selected concentrations.

| T/B | Rev. | % Loss | T/B | Rev. | % Loss |
| --- | --- | --- | --- | --- | --- |
| T1-28 (x12) | 0 | 0.0 | T1-32 (x12) | 0 | 0.0 |
| | 100 | 3.5 | | 100 | 9.8 |
| | 200 | 7.4 | | 200 | 17.3 |
| | 300 | 10.7 | | 300 | 19.6 |
| | 400 | 14.8 | | 400 | 22.6 |
| | 500 | 17.4 | | 500 | 24.9 |
| T3-28 (x14) | 0 | 0.0 | T3-32 (x14) | 0 | 0.0 |
| | 100 | 4.8 | | 100 | 3.3 |
| | 200 | 8.7 | | 200 | 7.0 |

TABLE 5-continued

Summary of Los Angeles Abrasion Value for selected treatment methods at selected concentrations.

| T/B | Rev. | % Loss | T/B | Rev. | % Loss |
| --- | --- | --- | --- | --- | --- |
| | 300 | 14.9 | | 300 | 10.8 |
| | 400 | 17.5 | | 400 | 13.4 |
| | 500 | 20.3 | | 500 | 15.4 |
| T6-28 (x20) | 0 | 0.0 | T6-32 (x20) | 0 | 0.0 |
| | 100 | 4.2 | | 100 | 4.4 |
| | 200 | 7.3 | | 200 | 7.0 |
| | 300 | 11.4 | | 300 | 9.9 |
| | 400 | 12.2 | | 400 | 12.9 |
| | 500 | 13.8 | | 500 | 15.8 |

T/B: Treatment and type of bacteria
Rev: Number of revolutions

Characterization of the Precipitates

Example 4—X-Ray Diffraction

Figure 3:
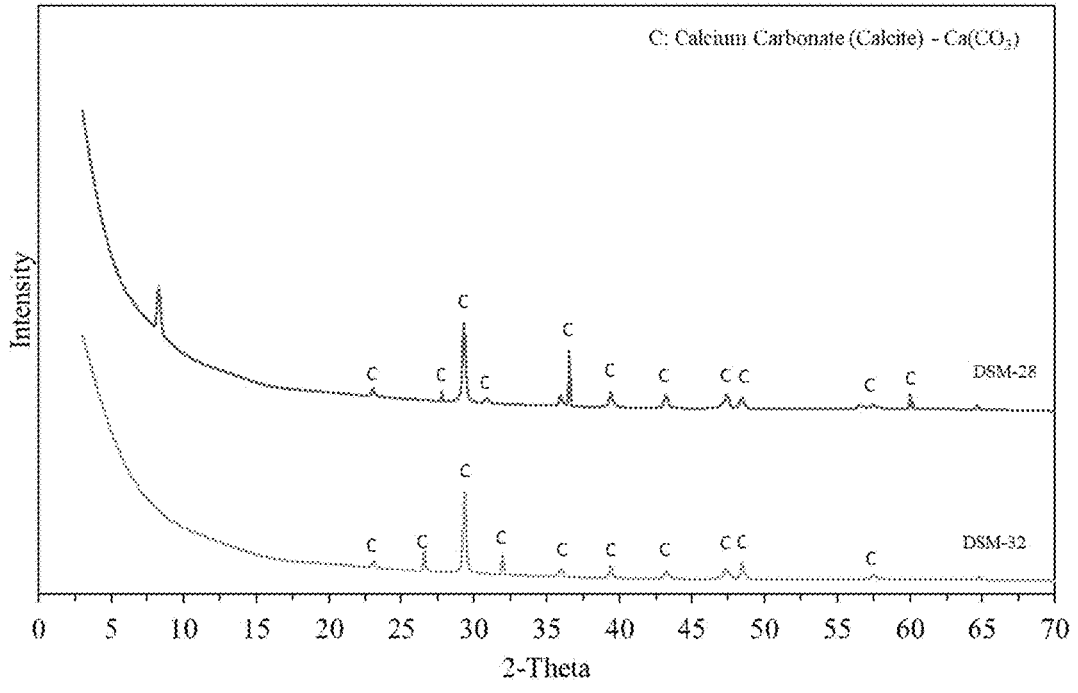
FIG. 3 provides XRD spectrum of the precipitate obtained from the surface of the RCA treated with DSM 28 and DSM 32.

FIG. 3 illustrates the XRD spectra of the precipitate material obtained from the surface of the treated RCA following treatment 6 (superlative treatment based on mass gain) using DSM 28 and DSM 32. The main identified compound in RCA treated using DSM 28 and DSC 32 was calcite, with peaks at 23, 26, 29, 31, 37, 39, 43, 47.5, 48, 57, and 60° 2θ. The most pronounced peak was recorded at 29° 2θ. This confirms that the treatment of RCA resulted in the formation of calcium carbonate on its surface.

Example 5—Scanning Electron Microscopy

Figure 4:
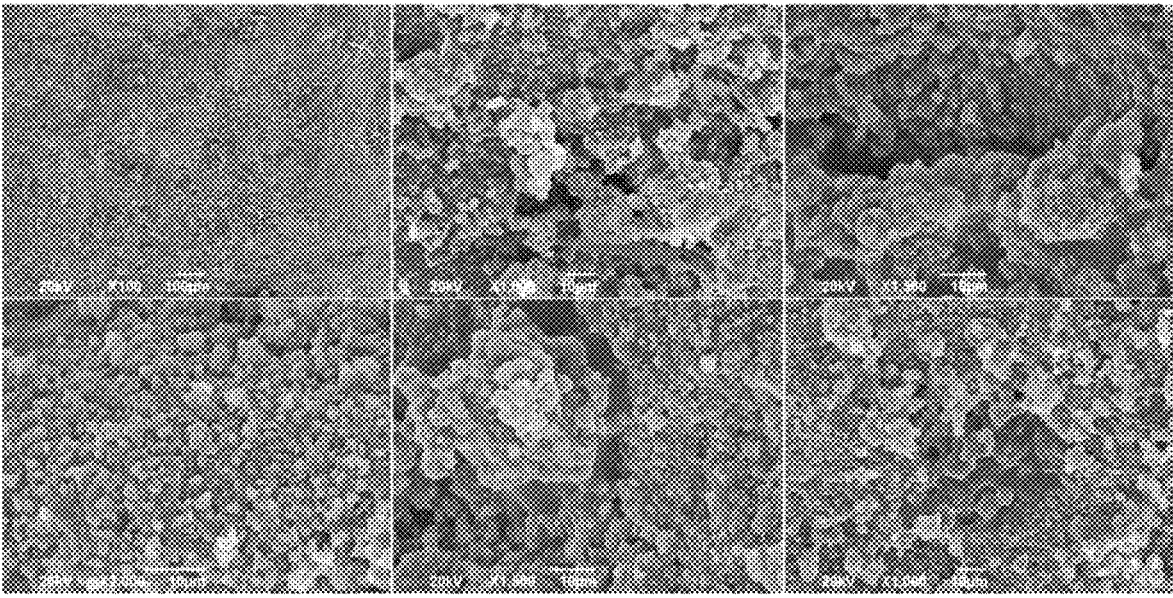
FIG. 4 provides SEM for samples treated with DSM 28.
Figure 5:
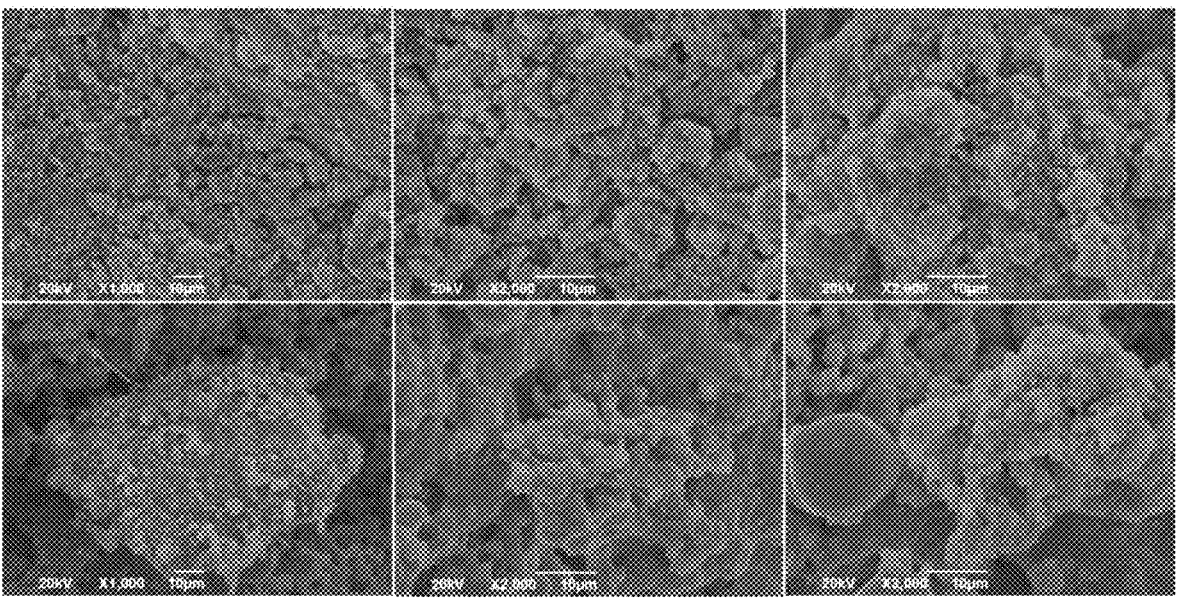
FIG. 5 provides SEM for samples treated with DSM 32.

The morphology of treated RCA samples was examined using SEM analysis, as shown in the micrographs of FIG. 4 and FIG. 5. Samples treated using treatment 6 were selected, as they experienced a superior enhancement in performance compared to other treatments. The electron dispersive X-ray (EDX) spot analyses reveal the formation of calcium carbonate, which have been pointed out in the SEM micrographs with grey arrows. Accordingly, the findings of the SEM analysis are aligned with those of the XRD analysis.

Materials and Methods

Preparation of the Immobilization Gel
Part 1: Bacteria Cultivation

The bacteria to be utilized in the treatment was first prepared. This treatment method uses two strains: *Lysinibacillus sphaericus* (DSM 28) and *Bacillus megaterium* (DSM 32). The bacteria were received in powder form and revived according to the instructions of the provider. Several glycerol stocks were created and kept in the fridge for future use in case of contamination of the growth medium. Such contamination consumes the nutrients that are meant for DSM 28 and DSM 32, which will reduce their reproducibility and count. After the initial revival step, the bacteria used in the treatment were obtained by sub-culturing. The bacteria used in the treatment were kept in a static incubator at 27° C. for a minimum of 10 days. The incubation duration was determined by obtaining samples of the cultures every day and testing their optical density (OD) using a spectrophotometer. Once the $OD_{600}$ value was greater or equal to 1, the cultures were deemed ready for the next step. Subsequently, the growth medium was transferred into centrifuge tubes under sterile conditions and centrifuged for 15 minutes at 5000 rpm. After the batches were centrifuged, the supernatant was discarded, and a vortex shaker was used to separate the bacteria pellets on the bottom of the tube. These pellets were collected in a small beaker and placed in the incubator.

Part 2: Preparation of Concentrated Batch

The nutrients and materials required for the bacteria to carry on the MICP process were prepared. Three different materials were identified and deemed necessary for the MICP process: nutrients, urea, and a calcium source. The nutrients were composed of peptone (5 g/L), sodium chloride (5 g/L), HM peptone B (equivalent to beef extract) (1.5 g/L), and yeast extract (1.5 g/L). For the treatment, the concentrated batch is referred to as the combination of nutrients, urea, and pure concentrated bacteria as described in Part 1. The concentrated batch was produced using different nutrients and urea concentrations. The base concentration (one-fold, ×1) was prepared using 13 g/L nutrients and 41.625 g/L urea. Calcium chloride was not mixed in the concentrated batch; instead, it was mixed separately with a similar concentration to that of urea (41.625 g/L). In addition to the base concentration of ×1, different concentrations were also used, including, ×2, ×4, ×6, ×8, ×10, ×12, ×14, ×16, and ×20. The purpose of examining different concentrations is to determine the optimum concentration that will yield the highest precipitation of calcium carbonate. A sample of the concentrations is listed in Table 6. The three components, i.e., nutrients, urea, and calcium chloride, were prepared to obtain the required concentration. Then, these three components were autoclaved for 15 minutes at a temperature of 121° C. and left to cool down to room temperature. The nutrients were then mixed with the urea solution, after which the bacteria were added. The final pH value of the concentrated batch was measured using a pH meter to be in the range of 8.0 and 9.0.

TABLE 6

A sample of materials quantity required to obtain the desired concentration.

| | Materials (g/L) | | | |
|---|---|---|---|---|
| Concentration | Nutrients | CaCl$_2$ | Urea | Alginate |
| Base (×1.0) | 13.0 | 41.6 | 41.6 | 5% w/v |
| ×0.5 | 7.5 | 20.8 | 20.8 | |
| ×2.0 | 26.0 | 83.3 | 83.3 | |
| ×4.0 | 52.0 | 166.5 | 166.5 | |
| ×20.0 | 260.0 | 832.5 | 832.5 | |

Part 3: Preparation of Immobilization Gel

The immobilization gel utilized in this treatment was made of sodium alginate at a weight by volume (w/v) percentage of 5% (i.e., for every 100 mL of solution, 5 grams of sodium alginate was used). The immobilization gel was prepared by autoclaving deionized (DI) water for 15 minutes at 121° C. Then, the water was combined with the sodium alginate in a blender. Subsequently, the mix was allowed to cool to reach room temperature and dissipate the bubbles. It was then combined with the concentrated batch at a volumetric ratio of 1:1.

Part 4: Recycled Concrete Aggregates Preparation

The as-received RCA were processed in preparation for treatment. First, the as-received RCA were sieved to obtain aggregates with a particle size larger than 5 mm. The resulting sieved aggregates were washed with tap water to remove dust and other loose particles. After washing, RCA were placed in an oven at 105° C. for 24 hours to obtain oven-dry conditions. These steps were necessary to ensure accurate mass measurements, as shown in later sections.

Experimental Testing Program

Mass Gain

RCA are porous in nature. The MICP treatment process is hypothesized to reduce such porosity due to the formation and precipitation of calcium carbonates. To evaluate the effectiveness of the six (6) MICP treatment techniques, the mass gain method was used. The percentage change in mass before and after treatment is referred to as the mass gain and is calculated using Eq. 1. Results were compared to those of the NA.

$$\text{Mass gain (\%)} = \left[(M_2 - M_1)/M_1 \times 100\right] \qquad \text{(Eq. 1)}$$

Where $M_1$ is the oven-dry mass of the aggregates before treatment, and $M_2$ is the oven-dry mass of the aggregates after treatment.

Water Absorption

As the microbially induced calcium carbonate precipitation serves to reduce the porosity of the RCA, its water absorption is expected to decrease. As such, to measure the effectiveness of the MICP in treating the RCA, its water absorption was measured. The water absorption is calculated using Eq. 2. Results were compared to those of the NA.

$$\text{Water absorption (\%)} = \left[(W_2 - W_1)/W_1\right] \times 100 \qquad \text{(Eq. 2)}$$

Where $W_2$ is the saturated surface dry mass of the aggregates after 24 hours of soaking in water, while $W_1$ is the oven-dry mass of the aggregates.

Impact and Abrasion Resistance

The impact and abrasion resistance of the treated RCA was measured using a Los Angeles abrasion machine. It is a measure of the degradation of aggregates resulting from a combination of actions, including abrasion or attrition, impact, and grinding in a rotating steel drum. In their untreated, as-received state, RCA are more fragile than NA. Yet, it is expected that the MICP treatment would improve the RCA due to the anticipated lower porosity. To measure the abrasion resistance, Eq. 3 is used, where Y is the initial aggregate mass and C is the final aggregate mass after 500 revolutions. A higher mass loss was indicative of lower abrasion resistance. Results were compared to those of the NA.

$$\text{Loss (\%)} = \left[(C - Y)/C\right] \times 100 \qquad \text{(Eq. 3)}$$

Characterization of the Precipitate

The precipitated material on the surface of the treated RCA was characterized using various analytical tools. After drying, a powder sample was collected from the surface of the RCA treated with MICP treatment #5.The obtained sample was analyzed by Rigaku MiniFlex tabletop X-Ray diffractometer equipped with a CuKα _radiation tube (1=1.542 Å). The diffractometer was used to record the powder X-ray diffraction (XRD) patterns. The MiniFlex runs at 40 kV with an angle range of 3-90° (2θ) at a rate of 2° C. min-1.

The surface morphology of the treated RCA (treatment #5) was observed using a JEOL JSM-6390A scanning electron microscope (SEM). Samples were initially dried in an oven at 110±5° C. for 24 hours before they were gold coated with a JFC-1600 auto fine coater. After sputter-coating with a thin conductive gold layer (99% purity), treated RCA samples (25 mm in diameter) were analyzed in high-vacuum mode.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

What is claimed is:

1. A method for enhancing the properties of recycled concrete aggregates (RCA) by microbial-induced calcite precipitation, comprising:

applying to the RCA in two consecutive steps, in any order:

(i) an immobilization gel comprising sodium alginate at 4% to 6% by weight per volume, urea, nutrients comprising peptone, HM peptone B, yeast extract and sodium chloride, and a bacterial strain selected from *Lysinibacillus sphaericus* or *Priestia megaterium*, wherein the bacterial strain is provided in lyophilized form and rehydrated in the immobilization gel immediately prior to application, and (ii) a calcium chloride solution, wherein urea and calcium chloride are provided at a 1:1 molar ratio during treatment, and wherein urea and calcium chloride are each initially provided at a base concentration of 41.6 g/L±2% with stepwise increases up to 582.8 to 832.5 g/L while maintaining the 1:1 molar ratio, and wherein water absorption of the resulting RCA ranges from 0.5% to 3.0%, and Los Angeles abrasion mass loss measured after 500 revolutions ranges from 15% to 21%.

2. The method of claim 1, wherein the bacterial strain is *Lysinibacillus sphaericus*.

3. The method of claim 1, wherein the bacterial strain is *Priestia megaterium*.

4. The method of claim 1, wherein calcite precipitation occurs in an alkaline medium at a pH of least 9 and at a temperature of 20 to 25° C.

5. The method of claim 1, wherein the two consecutive steps comprise spraying RCA with the immobilization gel and spraying the calcium chloride solution in sequence.

6. The method of claim 1, wherein the two consecutive steps comprise spraying RCA with the immobilization gel and soaking in the calcium chloride solution in sequence.

7. The method of claim 1, wherein the two consecutive steps comprise soaking RCA in the immobilization gel and soaking in the calcium chloride solution in sequence.

8. The method of claim 1, wherein the two consecutive steps comprise soaking RCA in the immobilization gel and spraying the calcium chloride solution in sequence.

9. The method of claim 1, wherein the two consecutive steps comprise spraying RCA with the calcium chloride solution and soaking in the immobilization gel in sequence.

10. The method of claim 1, wherein the two consecutive steps comprise soaking RCA in the calcium chloride solution and spraying the immobilization gel in sequence.

11. The method of claim 1, further comprising a step of soaking RCA in the calcium chloride solution, wherein soaking in the calcium chloride solution lasts 12 to 24 hours under static conditions.

12. The method of claim 1, wherein each of peptone, HM peptone B, and yeast extract is present at 2% to 5% by weight per volume and sodium chloride is present at 0.5% to 3% by weight per volume in the immobilization gel.

13. The method of claim 1, wherein size of the RCA is at least 5 millimeters and less than 25 millimeters.

14. The method of claim 1, wherein, before the first of the two steps, the RCA is rinsed with water to remove loosely attached fines or dirt.

* * * * *